US005789198A

United States Patent [19]

Akerblom

[11] Patent Number: 5,789,198
[45] Date of Patent: Aug. 4, 1998

[54] HUMAN LEPTIN RECEPTOR-RELATED PROTEIN

[75] Inventor: Ingrid E. Akerblom, Redwood City, Calif.

[73] Assignee: Incyte Pharmaceuticals, Inc., Palo Alto, Calif.

[21] Appl. No.: 691,071

[22] Filed: Aug. 1, 1996

[51] Int. Cl.$^6$ .................. C12N 15/12; C12N 15/85
[52] U.S. Cl. ............... 435/69.1; 435/172.3; 435/320.1; 435/325; 536/23.5
[58] Field of Search ............... 536/23.5; 435/320.1, 435/325, 69.1, 172.3

[56] References Cited

FOREIGN PATENT DOCUMENTS

WO96/086510  3/1996  WIPO.

OTHER PUBLICATIONS

Hillier L, et al. "yh73d04.r1 Homo sapiens cDNA clone 135367 5 prime." ETS Database Accession No. R32609, Apr. 28, 1995.

Hillier L, et al. "za11a11.s1 Homo sapiens cDNA clone 292220 3 prime." ETS Database Accession No. N62459, Mar. 1, 1996.

Thompson DB, et al. "Human leptin receptor (LEPR) gene, exon 2." Genbank Database Accession No. U59247, May 24, 1996.

Stratagene Catalog, p. 172, 1995.

Sambrook J, et al. "Molecular Cloning: A Laboratory Manual." Cold Spring Harbor Laboratory Press, NY, pp. 8.46–8.52, 1989.

Darnell J, et al. "Molecular Cell Biology." Scientific American Books, Inc., NY, p. 255, 1986.

Chehab, F.F., et al., "Correction of the sterility defect in homozygous obese female mice by treatment with the human recombinant leptin" Nature Genetics, 12:318–320 (1996).

Chen, H., et al., "Evidence That the Diabetes Gene Encodes the Leptin Receptor: Identification of a Mutation in the Leptin Receptor Gene in db/db Mice" Cell, 84:491–495 (1996).

Cioffi, J.A., et al., "Novel B219/OB receptor isoforms: Possible role of leptin in hematopoiesis and reproduction" Nature Medicine, 2:585–589 (1996).

Huang, M., et al., "Analysis of a 42.5 kb DNA Sequence of Chromosome X Reveals Three tRNA Genes and 14 New Open Reading Frames Including a Gene Most Probably Belonging to the Family of Ubiquitin–Protein Ligases" Yeast, 11:775–781 (1995).

Khachigian, L.M., et al., "Platelet–Derived Growth Factor and Alternative Splicing: A Review" Pathology, 24:280–290 (1992).

Lee, G.H., et al., "Abnormal splicing of the leptin receptor in diabetic mice" Nature, 379:632–635 (1996).

Phillips, M.S., et al., "Leptin receptor missense mutation in the fatty Zucker rat" Nat. Genet., 13:18–19 (1996).

Tartaglia, L.A., et al., "Identification and Expression Cloning of a Leptin Receptor, OB–R" Cell, 83:1263–1271 (1995).

Thomas, P.M., et al., "Mutations in the Sulfonylurea Receptor Gene in Familial Persistent Hyperinsulinemic Hypoglycemia of Infancy" Science, 268:426–429 (1995).

Wilson, R., et al., "2.2 Mb of contiguous nucleotide sequence from chromosome III of C. elegans" Nature, 368:32–38 (1994).

Zhang, Y., et al., "Positional cloning of the mouse obese gene and its human homologue" Nature, 372:425–432 (1994).

Marra, M. et al. (GI 1368126), GenBank Sequence Database (Accession W62925), National Center for Biotechnology Information, National Library of Medicine, Bethesda, Maryland, 20894.

Hillier, et al. (GI 1232038), GenBank Sequence Database (Accession N74753), National Center for Biotechnology Information, National Library of Medicine, Bethesda, Maryland, 20894.

Pelleymounter, M.A. et al., "Effects of the obese Gene Product on Body Weight Reduction in ob/ob Mice" Science (1995) 269:541–543.

Bailleaul, B. et al., "The leptin receptor promoter controls expression of a second distinct protein" Nuc.Acids Res. (1997) 25:2752–2758.

Primary Examiner—Douglas W. Robinson
Assistant Examiner—Amy T. Nelson
Attorney, Agent, or Firm—Incyte Pharmaceuticals, Inc.

[57] ABSTRACT

The present invention provides a polynucleotide which identifies and encodes a novel human leptin receptor-related protein (LRRP). The invention provides for genetically engineered expression vectors and host cells comprising the nucleic acid sequence encoding LRRP.

7 Claims, 8 Drawing Sheets

```
5' TCT GGC TTG GGC AGG CTG CCC GGG CCG TGG CAG GAA GCS GGA AGC AGC CGC GGC
                    9              18             27             36             45             54

CCC AGT TCG GGA GAC ATG GCG GGC GTT AAA GCT CTC GTG GCA TTA TCC TTC AGT
                   63             72             81             90             99            108
                                    M   A   G   V   K   A   L   V   A   L   S   F   S

GGG GCT ATT GGA CTG ACT TTT CTT ATG CTG GGA TGT GCC TTA TCC TTC GAG GAT
                  117            126            135            144            153            162
    G   A   I   G   L   T   F   L   M   L   G   C   A   L   S   F   E   D

GTT TAC CCC TTA TTC GTC CTG ATT TTC CAC GGC ATC TCC CCC ATC CCC CAT
                  171            180            189            198            207            216
    V   Y   P   L   F   V   L   I   F   H   G   I   S   P   I   P   H

TTC ATT GCC AAA AGA ACC TAT GTC ACC TAT TTC GTT TCT GCC TGT AGT GCC TGT CGG
                  225            234            243            252            261            270
    F   I   A   K   R   T   Y   V   T   Y   F   V   S   A   C   S   A   C   R

TTC ATT GCC TAT TTC TTC ACT ACT ACT GGA ATT GTT GTT TCT GCC TTT GGA TTT CCT
                  279            288            297            306            315            324
    E   L   A   Y   F   F   T   T   T   G   I   V   V   S   A   F   G   F   P
```

FIGURE 1A

```
       333             342             351             360             369             378
GTT ATT CTT GCT CGT GTG GCT GTG ATC AAA TGG GGA GCC TGC GGC CTT GTG TTG
 V   I   L   A   R   V   A   V   I   K   W   G   A   C   G   L   V   L 387             396             405             414             423             432
GCA GGC AAT GCA GTC ATT TTC CTT ACA ATT CAA GGG TTT TTC CTT ATA TTT GGA
 A   G   N   A   V   I   F   L   T   I   Q   G   F   F   L   I   F   G 441             450             459             468             477             486
AGA GGA GAT GAT TTT AGC TGG GAG CAG TGG TAG CAC TTT ATT CTG ATT ACA GTG
 R   G   D   D   F   S   W   E   Q   W 495             504             513             522             531             540
CAT TGA ATT TCT TAG AAC TCA TAC TAT CTG TAT ACA TGT GCA CAT GCG GCA TTT 549             558             567             576             585             594
TAC TAT GAA ATT TAA TAT GCT GGG TTT TTT AAT ACC TTT ATA TAT CAT GTT CAC 603             612             621             630             639             648
TTT AAG AAA GAC TTC ATA AGT AGG AGA TGA GTT TTA TTC TCA GCA AAT AGA CCT
```

FIGURE 1B

```
     657     666     675     684     693     702
GTC AAA TTT AGA TTA TGT TAC TCA AAT TAT GTT ACT TGT TTG GCT GTT CAT GTA 711     720     729     738     747     756
GTC ACG GTG CTC TCA GAA AAT ATA TTA ACG CAG TCT TGT AGG CAG CTG CCA CCT 765     774     783     792     801     810
TAT GCA GTG CAT CGA AAC CTT TTG GGG GAT GTG CTT GGA GAG GCA GAT AAC 819     828     837     846     855     864
GCT GAA GGC CTC TCA TGA CCC AGG AAG GCC GGG GTG GWT CCC TCT TTK TTT

873
TGT AGT CCA  3'
```

FIGURE 1C

The Electronic Northern for Clone: 492703
and Stringency >= 50

| Library | Lib Description | Abun | Pct Abun |
|---|---|---|---|
| RATRNOT01 | heart, right atrium, 51 F | 1 | 0.0861 |
| SYNORAB01 | synovium, hip, rheumatoid, 68 F | 4 | 0.0779 |
| LIVRNOM01 | liver, 49 M, WM | 1 | 0.0254 |
| PLACNOB01 | placenta, neonatal F | 1 | 0.0225 |
| BRSTNOT01 | breast, 56 F | 1 | 0.0192 |
| HNT2AGT01 | hNT-2 cell line, post-mitotic neurons | 1 | 0.0190 |
| HNT2NOT01 | hNT-2 cell line, teratocarcinoma, control | 1 | 0.0172 |
| BRSTTUT03 | breast tumor, 58 F, match to BRSTNOT05 | 1 | 0.0148 |
| COLNFET02 | colon, fetal F | 1 | 0.0142 |
| UCMCL5T01 | lymphocytes (umbilical cord), treated IL-5 | 1 | 0.0125 |
| MELANOM01 | melanocytes, M, NORM, WM | 1 | 0.0108 |
| PLACNOM02 | placenta, neonatal F, NORM, WM | 1 | 0.0056 |

FIGURE 2

* Numbering relative to human leptin receptor
  Hatched area represents identical sequences

```
                                                                    SEQ ID NO-1
                                                                    SEQ ID NO-3
                                                                    SEQ ID NO-4

HUMAN LEPTIN RECEPTOR-RELATED PROTEIN

FIELD OF THE INVENTION

The present invention relates to nucleic acid and amino acid sequences of a novel human leptin receptor-related protein and to the use of these sequences in the diagnosis, study, prevention and treatment of disease.

BACKGROUND OF THE INVENTION

The obese (ob) gene product, leptin, is important circulating signal for the regulation of body weight (Zhang Y et al (1994) Nature 372: 425–432). Mice homozygous for a nonfunctional ob gene become morbidly obese and diabetic, due to overeating and increased metabolic efficiency. In 1995, Tartaglia L A et al (Cell 83: 1263–1271) described a high affinity receptor for murine leptin (OB-R). Evidence suggests that the weight-reducing effects of leptin may be mediated by signal transduction through OB-R in the hypothalamus (Lee G H et al (1996) Nature 379: 632–635).

Regulation in the expression of splice variants can have a important role in the activity of signal transduction molecules and has been implicated in the pathogenesis of several diseases (Khachigian L M et al (1992) Pathology 24: 280–290). For example, mutations that create new splice variants of the sulfonylurea receptor gene segregate with familial persistent hyperinsulinemic hypoglycemia (Thomas P M et al (1995) Science 268: 426–429).

At least 9 alternatively spliced forms of mouse OB-R have been described (Lee et al, supra). A splice variant, B219, is expressed in the mouse yolk sac, early fetal liver, enriched hematopoietic stem cells, a variety of lympho-hematopoietic cells lines, and in adult reproductive organs and may be directly involved in hematopoiesis and reproduction (Cioffi J A et al (1996) Nature Medicine 2: 585–589). Additional support for leptin and a leptin receptor role in reproduction comes from Chehab F F et al, who report that treatment with leptin corrects a sterility defect in ob/ob female mice (1996, Nature Genet 12: 318–320). The researchers showed that leptin brings on fertility by restoring necessary hypothalmic and pituitary hormone levels rather than by fat reduction.

An OB-R mutation that creates an alternatively spliced transcript is responsible for the severely obese phenotype of db/db mice (Chen H et al (1996) Cell 84: 491–495). Based on synteni between human and mouse chromosomes, the human version of OB-R is likely to map to human chromosome 1p31 (Lee et al, supra).

Genome sequencing efforts in *Caenorhabditis elegans* and *Saccharomyces cerevisiae* have revealed putative open reading frames (ORFs) C30B5.2 and YJR044c, respectively (Wilson R et al, (1994) Nature 368: 32–38; Huang M E et al (1995) Yeast 11: 775–781). YJR044c and C30B5.2 are 27% identical and 71% similar in amino acid sequence and share a similar pattern of hypdrophobicity. YJR044c has been characterized as a putative membrane associated protein (Wilson et al, supra). The C30B5.2 amino acid sequence has a consensus pattern (CCxxHxxC) for phospholipase A2, a family of enzymes that release fatty acids from the second carbon group of glycerol.

The activity of many signal transduction molecules, such as the leptin receptor, is thought to be regulated by the expression of splice variants of the molecule. A new leptin receptor-related protein could provide the basis for diagnosis and treatment of disease states related to signal transduction events associated with metabolic disorders, such as obesity and diabetes, and reproductive disorders, including infertility.

SUMMARY

The present invention discloses a novel human leptin receptor-related protein (hereinafter referred to as LRRP), characterized as having homology to the membrane associated proteins of *C. elegans* ORF C30B5.2 (GI 733555) and *S. cerevisiae* ORF YJR044c (GI 1197072) and sharing part of its nucleic acid coding sequences with a non-coding region of human leptin receptor cDNA (GI 1139595). Accordingly, the invention features a substantially purified leptin receptor-related protein, as shown in the amino acid sequence of SEQ ID NO:1. The invention also relates to a polypeptide as shown in SEQ ID NO:1 from Met$_{22}$ through Trp$_{131}$, as well as other fragments of SEQ ID NO:1.

One aspect of the invention features isolated and substantially purified polynucleotides which encode LRRP. In a particular aspect, the polynucleotide is the nucleotide sequence of SEQ ID NO:2. In addition, the invention features polynucleotide sequences that hybridize under stringent conditions to a fragment of SEQ ID NO:2, from nucleotides A$_{163}$ to A$_{874}$, inclusive.

The invention further relates to nucleic acid sequence encoding LRRP, oligonucleotides, peptide nucleic acids (PNA), fragments, portions or antisense molecules thereof, and expression vectors and host cells comprising polynucleotide sequences encoding LRRP. The present invention also relates to antibodies which bind specifically to LRRP, pharmaceutical compositions comprising substantially purified LRRP, fragments thereof, or alternatively, antagonists of LRRP, in conjunction with a suitable pharmaceutical carrier, and methods for producing LRRP, fragments thereof, or antagonists of LRRP.

BRIEF DESCRIPTION OF THE FIGURES

FIGS. 1A–1C show the amino acid sequence (SEQ ID NO:1) and nucleic acid sequence (SEQ ID NO:2) of the novel leptin receptor-related protein, LRRP produced using MacDNAsis software (Hitachi Software Engineering Co Ltd).

FIG. 2 shows the northern analysis for Incyte Clone 492703 (SEQ ID NO:2) produced electronically using LIFESEQ™ database (Incyte Pharmaceuticals, Palo Alto Calif.). The percentage abundance is calculated by multiplying the number of transcripts found in the library times 100 and dividing the product by the total number of transcripts in the library.

FIG. 4 shows the amino acid sequence alignments among LRRP (SEQ ID NO:1), *C. elegans* ORF C30B5.2 (GI 733555; SEQ ID NO:3), and *S. cerevisiae* ORF YJR044c (GI 1197072; SEQ ID NO:4) produced using the multisequence alignment program of DNAStar software (DNAStar Inc. Madison Wis.).

DETAILED DESCRIPTION OF THE INVENTION

Definitions

Figure 3:
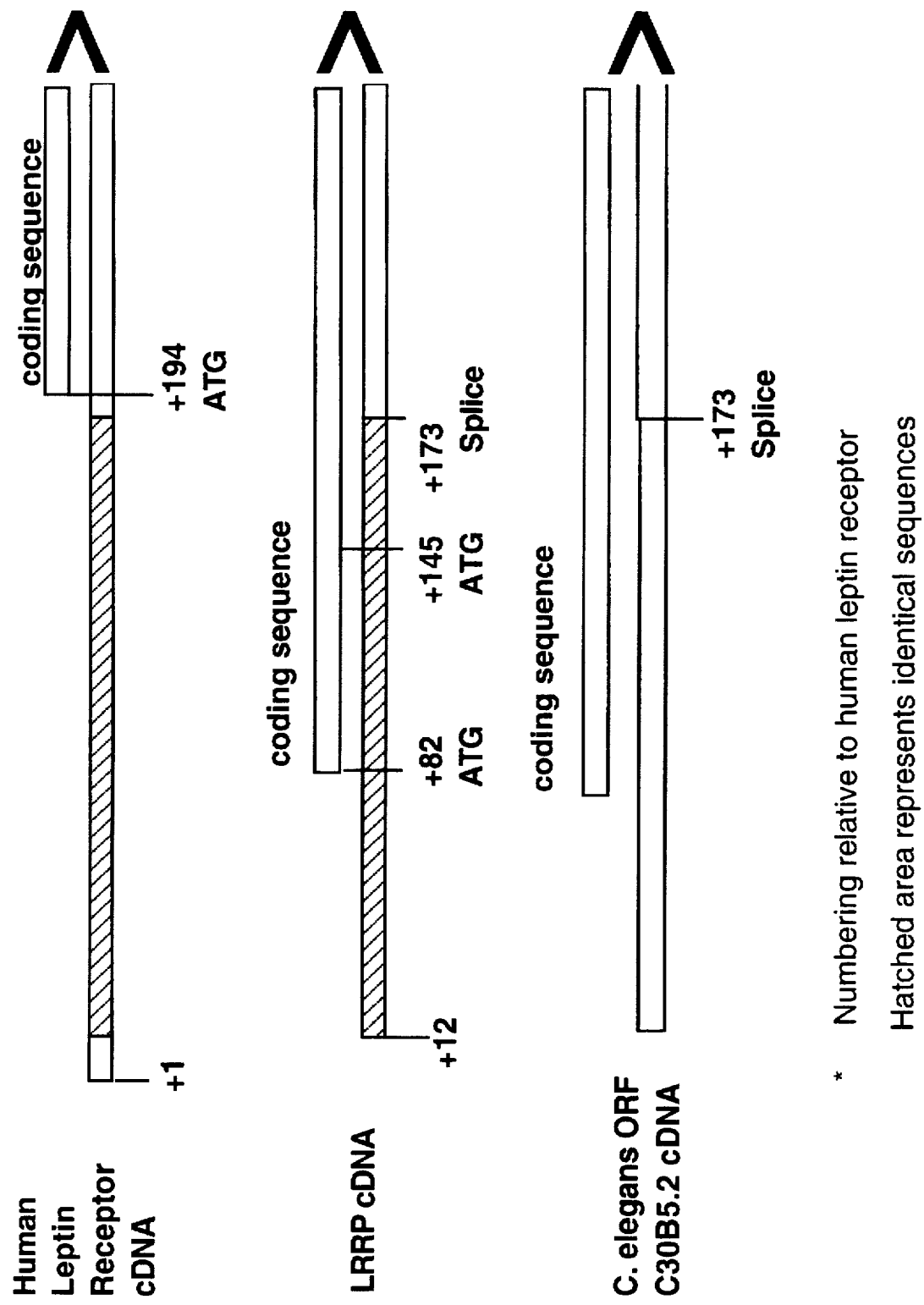
FIG. 3 shows a schematic diagram of the cDNAs of human leptin receptor, LRRP, and *C. elegans* ORF C30B5.2, highlighting similarities and differences in selected splice sites and coding sequences.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, LRRP refers to the amino acid sequence of substantially purified LRRP obtained from any species, particularly mammalian, including bovine, ovine, porcine, murine, equine, and preferably human, from any source whether natural, synthetic, semi-synthetic or recombinant.

A "variant" of LRRP is defined as an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to an LRRP having structural, regulatory or biochemical functions of a naturally occurring LRRP. Likewise, "immunologically active" defines the capability of the natural, recombinant or synthetic LRRP, or any oligopeptide thereof, to induce a specific immune response in appropriate animals or cells and to bind with specific antibodies.

The term "derivative" as used herein refers to the chemical modification of a nucleic acid encoding LRRP or the encoded LRRP. Illustrative of such modifications would be replacement of hydrogen by an alkyl, acyl, or amino group. A nucleic acid derivative would encode a polypeptide which retains essential biological characteristics of natural LRRP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm-5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach C W and G S Dveksler (1995, *PCR Primer, a Laboratory Manual*, Cold Spring Harbor Press, Plainview N.Y.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring LRRP.

A "substitution" results from the replacement of one or more nucleotides or amino acids by different nucleotides or amino acids, respectively.

Description

The present invention relates to a novel human leptin receptor-related protein initially identified among the cDNAs from a hNT2 cell line cDNA library (HNT2NOT01) and to the use of the nucleic acid and amino acid sequences in the study, diagnosis, prevention and treatment of disease states related to signal transduction events associated with metabolic disorders, such as obesity and diabetes, and reproductive disorders, including infertility. cDNAs encoding a portion of LRRP were found in cDNA libraries derived from the tissues and cell lines shown in FIG. 2. Portions of cDNAs unique to LRRP and portions of cDNAs unique to leptin receptor were found in an immortalized human adipocyte cell line (Strosberg A D, personal communication). Naturally occurring expression of LRRP is not necessarily limited to these cell and tissue types.

The present invention also encompasses LRRP variants. A preferred LRRP variant is one having at least 80% amino acid sequence similarity to the LRRP amino acid sequence (SEQ ID NO:1), a more preferred LRRP variant is one having at least 90% amino acid sequence similarity to SEQ ID NO:1 and a most preferred LRRP variant is one having at least 95% amino acid sequence similarity to SEQ ID NO:1.

Nucleic acid encoding the human leptin receptor-related protein of the present invention was first identified in cDNA, Incyte Clone 492703 (SEQ ID NO:2), through a computer-generated search for nucleic acid sequence alignments. The nucleic acid sequence of SEQ ID NO:2 encodes the LRRP amino acid sequence, SEQ ID NO:1 and shares some exons with the non-coding regions of human leptin receptor cDNAs (Tartaglia et al, supra; FIG. 3). Nucleotides $G_1$ to $G_{162}$ of SEQ ID NO:2 are identical to nucleotides $G_{12}$ to $G_{173}$ in the non-coding region of human leptin receptor cDNA (GI 1139595; Tartaglia et al, supra). The coding sequence of LRRP is unique. Nucleic acids at a putative splice site in LRRP, the 3' end of the region of identity with human leptin receptor, encode amino acids that align precisely with those encoded at a putative splice site for the related gene *C. elegans* ORF C30B5.2 (GI 733555; Wilson et al, supra; FIG. 3). An exon in the non-coding region of the rat leptin receptor cDNA (GI 1335914) has a high degree of homology to the portion of the LRRP coding sequence that matches the non-coding sequence of the human leptin receptor. The LRRP gene maps to the same site as the leptin receptor, human chromosome 1p31.

Figure 5:
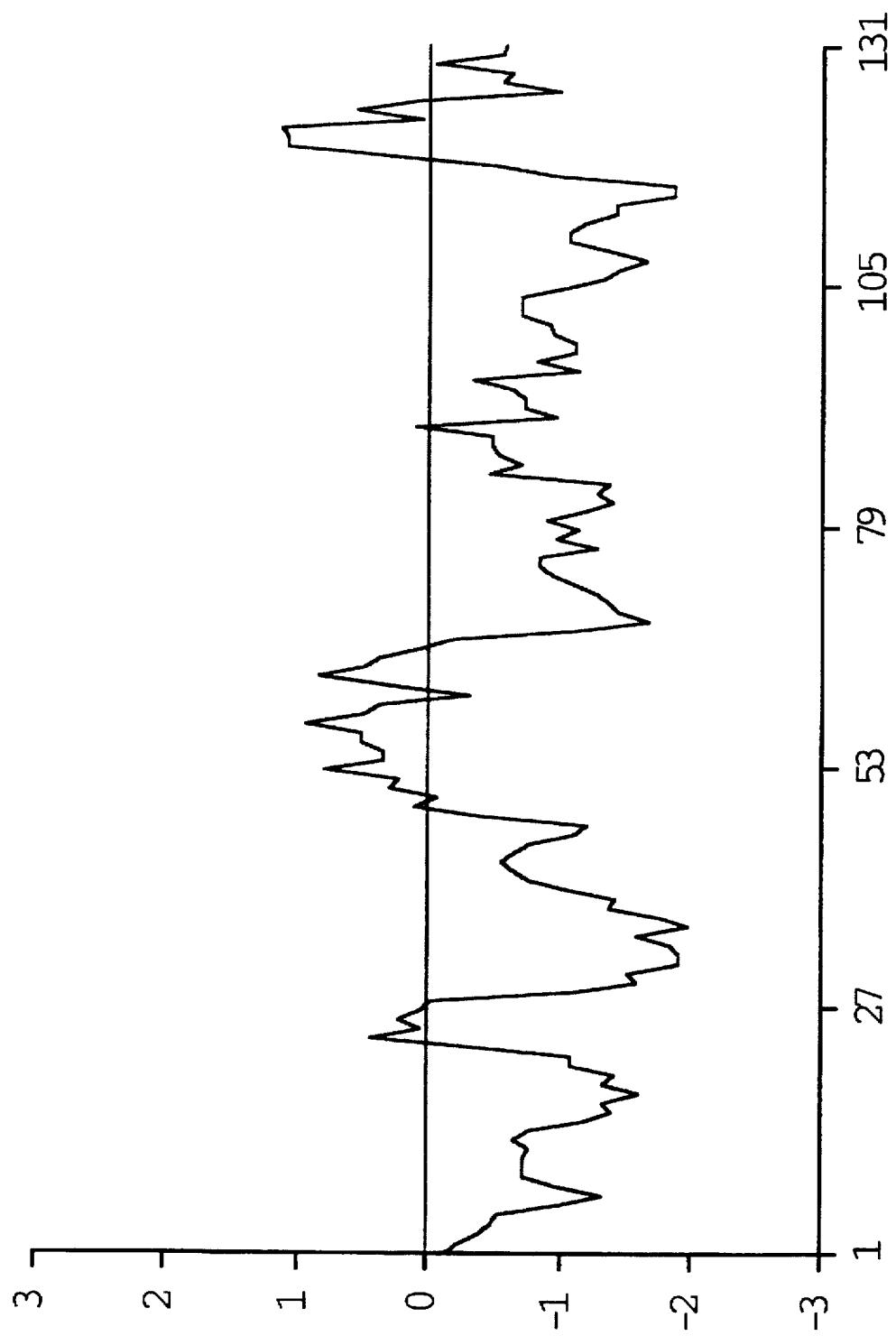
FIG. 5 shows the hydrophobicity plot (generated using MacDNAsis software) for LRRP, SEQ ID NO:1; the X axis reflects amino acid position, and the negative Y axis, hydrophobicity (FIGS. 5 and 6).
Figure 6:
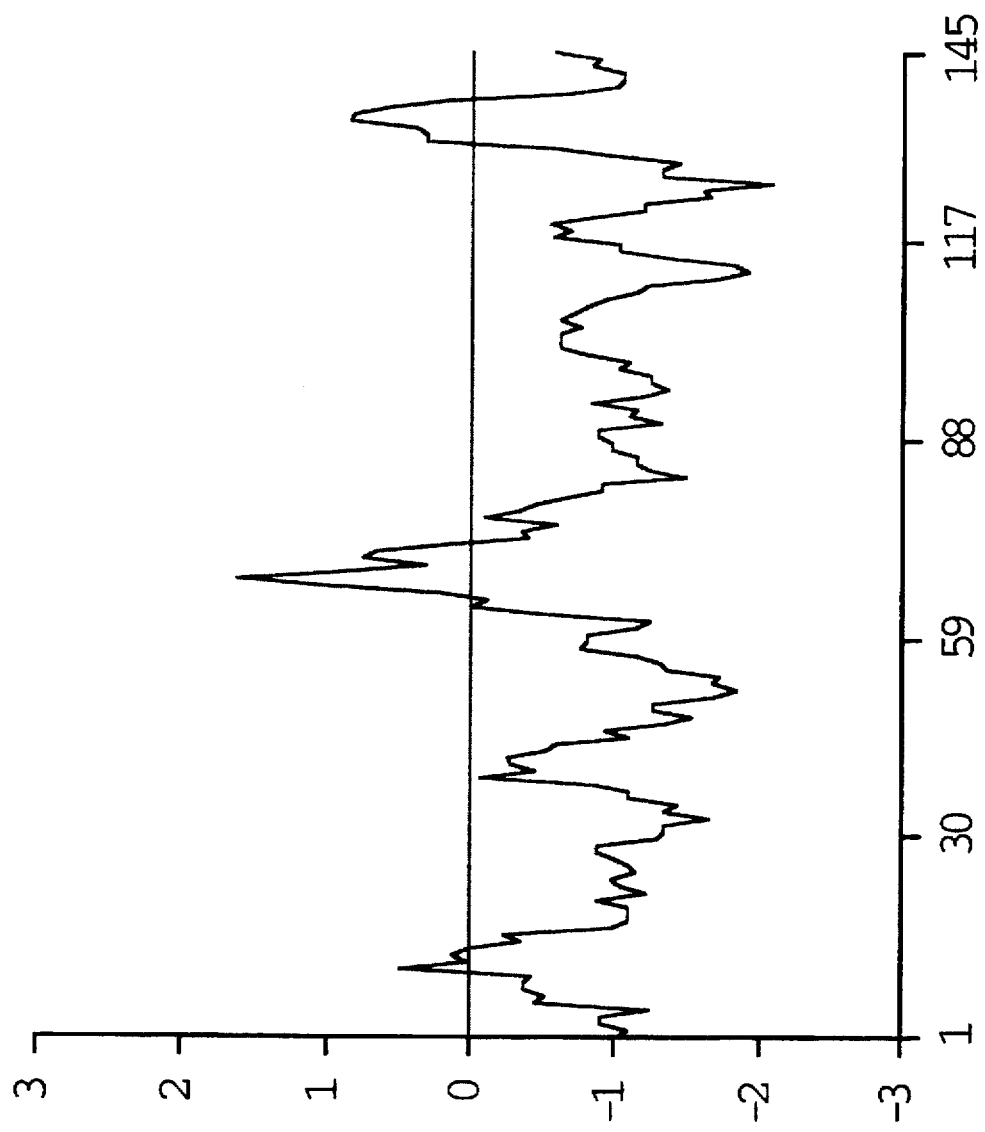
FIG. 6 shows the hydrophobicity plot for *C. elegans* ORF C30B5.2, SEQ ID NO:3.

In one embodiment of the present invention, translation of the LRRP mRNA starts at the ATG that begins at $A_{71}$ of SEQ ID NO:2. In another embodiment, translation of the LRRP mRNA starts at the following in-frame ATG that begins at $A_{134}$. The present invention is based, in part, on the chemical and structural homology among LRRP, *C. elegans* ORF C30B5.2 (GI 733555), and *S. cerevisiae* ORF YJR044c (GI 1197072; Huang et al, supra; FIG. 4). LRRP has 45% identity and 77% similarity to the amino acid sequence of *C. elegans* ORF C30B5.2. LRRP has 32% identity and 64% similarity to the amino acid sequence of *S. cerevisiae* ORF YJR044c. LRRP and the *C. elegans* ORF C30B5.2 hydrophobicity plots (shown in FIGS. 5 and 6) suggest LRRP shares configuration and membrane localization. The novel LRRP is 131 amino acids long and has no putative glycosylation sites.

The LRRP Coding Sequences

The nucleic acid and deduced amino acid sequences of LRRP are shown in FIGS. 1A and 1B. In accordance with the invention, any nucleic acid sequence which encodes the amino acid sequence of LRRP can be used to generate recombinant molecules which express LRRP. In a specific embodiment described herein, a nucleotide sequence encoding a portion of LRRP was first isolated as Incyte Clone 492703 from an hNT2 cell cDNA library (HNT2NOT01).

It will be appreciated by those skilled in the art that as a result of the degeneracy of the genetic code, a multitude of LRRP-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring LRRP, and all such variations are to be considered as being specifically disclosed.

Although nucleotide sequences which encode LRRP and its variants are preferably capable of hybridizing to the nucleotide sequence of the naturally occurring LRRP under appropriately selected conditions of stringency, it may be advantageous to produce nucleotide sequences encoding LRRP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding LRRP and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding an LRRP and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding LRRP or any portion thereof.

Also included within the scope of the present invention are polynucleotide sequences that are capable of hybridizing to the nucleotide sequence of FIGS. 1A and 1B, or fragments thereof, under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined stringency.

Altered nucleic acid sequences encoding LRRP which may be used in accordance with the invention include deletions, insertions or substitutions of different nucleotides resulting in a polynucleotide that encodes the same or a functionally equivalent LRRP. The protein may also show deletions, insertions or substitutions of amino acid residues which produce a silent change and result in a functionally equivalent LRRP. Deliberate amino acid substitutions may be made on the basis of similarity in polarity, charge, solubility, hydrophobicity, hydrophilicity, and/or the amphipathic nature of the residues as long as the biological activity of LRRP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of LRRP. As used herein, an "allele" or "allelic sequence" is an alternative form of LRRP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE® (US Biochemical Corp, Cleveland OH), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding LRRP may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc. Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J D et al (1991; Nucleic Acids Res 19:3055–60). Additionally, one can use PCR, nested primers and PromoterFinder libraries to walk in genomic DNA (PROMOTERFINDER™ Clontech, Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER™ and SEQUENCE NAVIGATOR™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode LRRP, fragments of the polypeptide, fusion proteins or functional equivalents thereof may be used in recombinant DNA molecules that direct the expression of LRRP in appropriate host cells. Due to the inherent degeneracy of the genetic code, other DNA sequences which encode substantially the same or a functionally equivalent amino acid sequence, may be used to clone and express LRRP. As will be understood by those of skill in the art, it may be advantageous to produce LRRP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of LRRP expression or to produce recombinant RNA transcripts having desirable properties, such as a longer half-life, than transcripts produced from naturally occurring sequence.

The nucleotide sequences of the present invention can be engineered in order to alter an LRRP coding sequence for a variety of reasons, including but not limited to, alterations which modify the cloning, processing and/or expression of the gene product. For example, mutations may be introduced using techniques which are well known in the art, eg. site-directed mutagenesis to insert new restriction sites, to alter glycosylation patterns, to change codon preference, to produce splice variants, etc.

In another embodiment of the invention, natural, modified or recombinant polynucleotides encoding LRRP may be ligated to a heterologous sequence to encode a fusion protein. For example, for screening of peptide libraries for inhibitors of LRRP activity, it may be useful to encode a chimeric LRRP protein that is recognized by a commercially available antibody. A fusion protein may also be engineered to contain a cleavage site located between an LRRP sequence and the heterologous protein sequence, so that the LRRP may be cleaved and purified away from the heterologous moiety.

In an alternate embodiment of the invention, the coding sequence of LRRP may be synthesized, whole or in part, using chemical methods well known in the art (see Caruthers M H et al (1980) Nuc Acids Res Symp Ser 215–23, Horn T et al (1980) Nuc Acids Res Symp Ser 225–32, etc). Alternatively, the protein itself could be produced using chemical methods to synthesize an LRRP amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg. Creighton (1983) *Proteins, Structures and Molecular Principles*, W H Freeman and Co, New York N.Y.). The composition of the synthetic peptides may be confirmed by amino acid analysis or sequencing (eg. the Edman degradation procedure; Creighton, supra). Additionally the amino acid sequence of LRRP, or any part thereof, may be altered during direct synthesis and/or combined using chemical methods with sequences from other proteins, or any part thereof, to produce a variant polypeptide.

Expression Systems

In order to express a biologically active LRRP, the nucleotide sequence encoding LRRP or its functional equivalent, is inserted into an appropriate expression vector, ie, a vector which contains the necessary elements for the transcription and translation of the inserted coding sequence.

Methods which are well known to those skilled in the art can be used to construct expression vectors containing an LRRP coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express an LRRP coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg. baculovirus); plant cell systems transfected with virus expression vectors (eg. cauliflower mosaic virus, CaMV; tobacco mosaic virus, TMV) or transformed with bacterial expression vectors (eg. Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUE-SCRIPT® phagemid (Stratagene, LaJolla Calif.) or PSPORT1 (Gibco BRL) and ptrp-lac hybrids and the like may be used. The baculovirus polyhedrin promoter may be used in insect cells. Promoters or enhancers derived from the genomes of plant cells (eg, heat shock, RuBIsCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of LRRP, vectors based on SV40 or EBV may be used with an appropriate selectable marker.

In bacterial systems, a number of expression vectors may be selected depending upon the use intended for LRRP. For example, when large quantities of LRRP are needed for the induction of antibodies, vectors which direct high level expression of fusion proteins that are readily purified may be desirable. Such vectors include, but are not limited to, the multifunctional E. coli cloning and expression vectors such as BLUESCRIPT® (Stratagene), in which the LRRP coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding LRRP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill Yearbook of Science and Technology (1992) McGraw Hill New York N.Y., pp 191–196 or Weissbach and Weissbach (1988) Methods for Plant Molecular Biology, Academic Press, New York N.Y., pp 421–463.

An alternative expression system which could be used to express LRRP is an insect system. In one such system, Autographa californica nuclear polyhedrosis virus (AcNPV) is used as a vector to express foreign genes in Spodoptera frugiperda cells or in Trichoplusia larvae. The LRRP coding sequence may be cloned into a nonessential region of the virus, such as the polyhedrin gene, and placed under control of the polyhedrin promoter. Successful insertion of LRRP will render the polyhedrin gene inactive and produce recombinant virus lacking coat protein coat. The recombinant viruses are then used to infect S. frugiperda cells or Trichoplusia larvae in which LRRP is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, an LRRP coding sequence may be ligated into an adenovirus transcription/translation complex consisting of the late promoter and tripartite leader sequence. Insertion in a nonessential E1 or E3 region of the viral genome will result in a viable virus capable of expressing LRRP in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of an LRRP sequence. These signals include the ATG initiation codon and adjacent sequences. In cases where LRRP, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express LRRP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt-cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the LRRP is inserted within a marker gene sequence, recombinant cells containing LRRP can be identified by the absence of marker gene function. Alternatively, a marker gene can be placed in tandem with an LRRP sequence under the control of a single promoter. Expression of the marker gene in response to induction or selection usually indicates expression of the tandem LRRP as well.

Alternatively, host cells which contain the coding sequence for LRRP and express LRRP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding LRRP can be detected by DNA-DNA or DNA-RNA hybridization or amplification using probes, portions or fragments of polynucleotides encoding LRRP. Nucleic acid amplification based assays involve the use of oligonucleotides or oligomers based on the LRRP-encoding sequence to detect transformants containing DNA or RNA encoding LRRP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of LRRP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on LRRP is preferred, but a competitive binding assay may be employed. These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to polynucleotides encoding LRRP include oligolabeling, nick translation, end-labeling or PCR amplification using a labeled nucleotide. Alternatively, the LRRP sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of LRRP

Host cells transformed with a nucleotide sequence encoding LRRP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding LRRP can be designed with signal sequences which direct secretion of LRRP through a prokaryotic or eukaryotic cell membrane. Other recombinant constructions may join LRRP to nucleotide sequence encoding a polypeptide domain which will facilitate purification of soluble proteins (Kroll D J et al (1993) DNA Cell Biol 12:441–53; cf discussion of vectors infra containing fusion proteins).

LRRP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and LRRP is useful to facilitate purification. One such expression vector provides for expression of a fusion protein compromising an LRRP and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying LRRP from the fusion protein.

In addition to recombinant production, fragments of LRRP may be produced by direct peptide synthesis using solid-phase techniques (cf Stewart et al (1969) Solid-Phase Peptide Synthesis, W H FREEMAN Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of LRRP may be chemically synthesized separately and combined using chemical methods to produce the full length molecule.

Uses of LRRP

The rationale for use of the nucleotide and polypeptide sequences disclosed herein is based in part on the the existence of shared exons between polynucleotides of the non-coding region of the leptin receptor (GI 1139595; Tartaglia et al, supra) and a portion of the coding region of LRRP; LRRP's pattern of gene expression; and chemical and structural homology among the novel human leptin receptor-related protein disclosed herein, the *C. elegans* ORF (GI 733555; Wilson et al, supra), and the *S. cerevisiae* ORF (GI 1197072; Huang et al, supra), genes that appear to be membrane localized.

Accordingly, LRRP or an LRRP derivative could provide the basis for diagnosis and treatment of disease states related to signal transduction events associated with metabolic disorders, such as obesity and diabetes, and reproductive disorders, including infertility. In those conditions where leptin receptor-related protein activity is not desirable, cells could be transfected with antisense sequences of LRRP-encoding polynucleotides or provided with inhibitors of LRRP.

LRRP Antibodies

LRRP-specific antibodies are useful for the diagnosis and treatment of conditions and diseases associated with expression of LRRP, with metabolic disorders, such as obesity and diabetes, and reproductive disorders, including infertility. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

LRRP for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of LRRP amino acids may be fused with those of another protein such as keyhole limpet hemocyanin and antibody produced against the chimeric molecule. Procedures well known in the art can be used for the production of antibodies to LRRP.

For the production of antibodies, various hosts including goats, rabbits, rats, mice, etc may be immunized by injection with LRRP or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to LRRP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce LRRP-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for LRRP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between LRRP and its specific antibody and the measurement of complex formation. A two-site, monoclonal-based immunoassay utilizing monoclonal antibodies reactive to two noninterfering epitopes on a specific LRRP protein is preferred, but a competitive binding assay may also be employed. These assays are described in Maddox D E et al (1983, J Exp Med 158:1211).

Diagnostic Assays Using LRRP Specific Antibodies

Particular LRRP antibodies are useful for the diagnosis of conditions or diseases characterized by expression of LRRP or in assays to monitor patients being treated with LRRP, agonists or inhibitors. Diagnostic assays for LRRP include methods utilizing the antibody and a label to detect LRRP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring LRRP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on LRRP is preferred, but a competitive binding assay may be employed. These assays are described, among other places, in Maddox, D E et al (1983, J Exp Med 158:1211).

In order to provide a basis for diagnosis, normal or standard values for LRRP expression must be established. This is accomplished by combining body fluids or cell extracts taken from normal subjects, either animal or human, with antibody to LRRP under conditions suitable for complex formation which are well known in the art. The amount of standard complex formation may be quantified by comparing various artificial membranes containing known quantities of LRRP with both control and disease samples from biopsied tissues. Then, standard values obtained from normal samples may be compared with values obtained from samples from subjects potentially affected by disease. Deviation between standard and subject values establishes the presence of disease state.

Drug Screening

LRRP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between LRRP and the agent being tested, may be measured.

Another technique for drug screening which may be used provides for high throughput screening of compounds having suitable binding affinity to the LRRP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of LRRP and washed. Bound LRRP is then detected by methods well known in the art. Purified LRRP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding LRRP specifically compete with a test compound for binding LRRP. In this manner, the antibodies can be used to detect the presence of any peptide which shares one or more antigenic determinants with LRRP.

Uses of the Polynucleotide Encoding LRRP

A polynucleotide encoding LRRP, or any part thereof, may be used for diagnostic and/or therapeutic purposes. In a preferred embodiment, the polynucleotide used for diagnostic purpose is from nucleotides $A_{163}$ to $A_{874}$ of SEQ ID NO:2. For diagnostic purposes, polynucleotides encoding LRRP of this invention may be used to detect and quantitate gene expression in biopsied tissues in which expression of LRRP may be implicated. The diagnostic assay is useful to distinguish between absence, presence, and excess expression of LRRP and to monitor regulation of LRRP levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding LRRP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring sequences encoding LRRP, alleles or related sequences.

Probes may also be used for the detection of related sequences and should preferably contain at least 50% of the nucleotides from any of these LRRP encoding sequences. The hybridization probes of the subject invention may be derived from the nucleotide sequence of SEQ ID NO:2 or from genomic sequence including promoter, enhancer elements and introns of the naturally occurring LRRP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding LRRP include the cloning of nucleic acid sequences encoding LRRP or LRRP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding LRRP or portions thereof may be used for the diagnosis of conditions or diseases with which the expression of LRRP is associated. For example, polynucleotide sequences encoding LRRP may be used in hybridization or PCR assays of fluids or tissues from biopsies to detect LRRP expression. The form of such qualitative or quantitative methods may include Southern or northern analysis, dot blot or other membrane-based technologies; PCR technologies; dip stick, pIN, chip and ELISA technologies. All of these techniques are well known in the art and are the basis of many commercially available diagnostic kits.

The nucleotide sequences encoding LRRP disclosed herein provide the basis for assays that detect signal transduction events associated with disease states or condition such as obesity, diabetes, and reproductive disorders. The nucleotide sequence encoding LRRP may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding LRRP in the sample indicates the presence of the associated disease or condition.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for LRRP expression must be established. This is accomplished by combining body fluids or cell extracts taken from normal subjects, either animal or human, with LRRP, or a portion thereof, under conditions suitable for hybridization or amplification. Standard hybridization may be quantified by comparing the values obtained for normal subjects with a dilution series of LRRP run in the same experiment where a known amount of a substantially purified LRRP is used. Standard values obtained from normal samples may be compared with values obtained from samples from patients afflicted with LRRP-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, as described in U.S. Pat. Nos. 4,683,195 and 4,965,188, provides additional uses for oligonucleotides based upon the LRRP sequence. Such oligomers are generally chemically synthesized, but they may be generated enzymatically or produced from a recombinant source. Oligomers generally comprise two nucleotide sequences, one with sense orientation (5→3') and one with antisense (3←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or calorimetric response gives rapid quantitation. For example, the presence of a relatively high amount of LRRP in extracts of biopsied tissues may indicate the onset of diabetes, obesity, or reproductive disorders. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use of Polynucleotide Sequences

Based upon LRRP's homology to genes encoding leptin receptor-related proteins that are believed to be membrane localized, its sharing of exons with the non-coding region of the leptin receptor, and its expression profile, polynucleotide sequences encoding LRRP or antisense polynucleotides could provide the basis for diagnosis and treatment of disease states related to signal transduction events associated with metabolic disorders, such as obesity and diabetes, and reproductive disorders, including infertility.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding LRRP. See, for example, the techniques described in Sambrook et al (supra) and Ausubel et al (supra).

The polynucleotides comprising full length cDNA sequence and/or its regulatory elements enable researchers to use sequences encoding LRRP as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding LRRP can be turned off by transfecting a cell or tissue with expression vectors which express high levels of a desired LRRP-encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of gene encoding LRRP. ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of sequences encoding LRRP.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding LRRP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for LRRP disclosed herein may be used in molecular biology techniques that have not yet been developed, provided the new techniques rely on properties of nucleotide sequences that are currently known, including but not limited to such properties as the triplet genetic code and specific base pair interactions.

Pharmaceutical Compositions

The present invention relates to pharmaceutical compositions which may comprise nucleotides, polypeptides, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of LRRP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg. of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg. ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

The examples below are provided to illustrate the subject invention and are not included for the purpose of limiting the invention.

EXAMPLES

I cDNA Library Construction

The hNT2 cell line exhibits characteristics of a committed neuronal precursor cell which is still at an early stage of development. The cDNA library for the untreated hNT2 cell line (HNT2NOT01, Cat. No. 937230) is available from Stratagene (Stratagene, La Jolla Calif.).

The library was constructed essentially as described below. Stratagene isolated the mRNA and prepared the cDNA library. cDNAs were primed using oligo d(T) and size fractionated to isolate fragments of 500 bp and larger. Synthetic adapter oligonucleotides were ligated onto the cDNA molecules enabling them to be inserted into the UNI-ZAP™ vector system (Stratagene). This allowed high efficiency unidirectional (sense orientation) lamda library construction and the convenience of a plasmid system with blue/white color selection to detect clones with cDNA insertions.

The quality of the cDNA library was screened using DNA probes, and then, the PBLUESCRIPT™ phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom constructed library phage particles were infected into $E.$ $coli$ host strain XL1-Blue (Stratagene). The high transformation efficiency of this bacterial strain increases the probability that the cDNA library contains rare, under-represented clones. Alternative unidirectional vectors include, but are not limited to, pcD-NAI (Invitrogen, San Diego Calif.) and pSHlox-1 (Novagen, Madison Wis.).

II Isolation of cDNA Clones

The phagemid forms of individual cDNA clones were obtained by employing the Miniprep Kit (Catalog No. 77468) available from Advanced Genetic Technologies Corp., Gaithersburg Md. This kit is in the 96-well format and provides enough reagents for 960 purifications. Each kit is provided with a recommended protocol, which was employed except for the following changes. First, the 96 wells were each filled with only 1 ml of sterile terrific broth with carbenicillin at 25 mg/L and glycerol at 0.4%. After the wells were inoculated, the bacteria were cultured for 24 hours and lysed with 60 μl of lysis buffer. A centrifugation step (2900 rpm for 5 minutes) was performed before the contents of the block were added to the primary filter plate. The optional step of adding isopropanol to TRIS buffer was not routinely performed. After the last step in the protocol, samples were transferred to a Beckman 96-well block for storage.

Alternatively, the in vivo excision process, in which the host bacterial strain is co-infected with both the library phage and an f1 helper phage, for purifying phagemid. Polypeptides or enzymes derived from both the library-containing phage and the helper phage nicks the DNA, initiates new DNA synthesis from defined sequences on the target DNA, and creates a smaller, single stranded circular phagemid DNA molecule that includes all DNA sequences of the PBLUESCRIPT™ phagemid and the cDNA insert. The phagemid DNA is released from the cells and purified, and used to reinfect fresh host cells (SOLR, Stratagene) where double stranded phagemid DNA is produced. Because the phagemid carries the gene for beta-lactamase, the newly transformed bacteria are selected on medium containing ampicillin.

Phagemid DNA may also be purified using the QIAWELL-8 Plasmid Purification System from the QIAGENDNA Purification System (QIAGEN Inc, Chatsworth Calif.). This product provides a convenient, rapid and reliable high-throughput method for lysing the bacterial cells and isolating highly purified phagemid DNA using QIAGEN anion-exchange resin particles with EMPORE™ membrane technology from 3M in a multiwell format. The DNA was eluted from the purification resin and prepared for DNA sequencing and other analytical manipulations.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul S F 1993 and 1990, supra) are used to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into acccount both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of LRRP-Encoding Polynucleotides to Full Length or to Recover Regulatory Elements Full length LRRP-encoding nucleic acid sequence (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known LRRP-encoding sequence "outward" generating amplicons containing new, unknown nucleotide sequence for the region of interest. The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| Step 1 | 94° C. for 1 min (initial denaturation) |
|--------|------------------------------------------|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94°C for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. In a preferred embodiment, hybridization probes are derived from sequences between nucleotides $A_{163}$ and $A_{874}$ of SEQ ID NO:2. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [Y-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®)

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The LRRP-encoding sequence, or any part thereof, is used to inhibit in vivo or in vitro expression of naturally occurring LRRP. Although use of antisense oligonucleotides, comprising about 20 base-pairs, is specifically described, essentially the same procedure is used with larger cDNA fragments. An oligonucleotide based on the coding sequence of LRRP, as shown in FIGS. 1A and 1B, is used to inhibit expression of naturally occurring LRRP. The complementary oligonucleotide is designed from the most unique 5' sequence as shown in FIGS. 1A and 1B and used either to inhibit transcription by preventing promoter binding to the upstream nontranslated sequence or translation of an LRRP-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A and 1B.

VIII Expression of LRRP

Expression of the LRRP is accomplished by subcloning the cDNAs into appropriate vectors and transfecting the vectors into host cells. In this case, the cloning vector, pSport, previously used for the generation of the cDNA library is used to express LRRP in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length LRRP-encoding sequence. The signal sequence directs the secretion of LRRP into the bacterial growth media which can be used directly in the following assay for activity.

IX LRRP Activity

LRRP activity can be assayed by measuring its effect on leptin receptor activity. Leptin receptor has characteristic JAK tyrosine kinase binding sites (Lee G H et al, supra; Fukunaga R et al (1991) EMBO J 10: 2855–2865). Activity of receptors which interact with JAK tyrosine kinases can be measured by evaluating $^{32}$P incorporation into protein following stimulation with the appropriate ligand (for example Wang Y et al (1995) Mol Endocrinol 9: 303–311).

LRRP's effect on leptin receptor activity can be assessed by measuring $^{32}$P incorporation following addition of leptin in cell lines transfected with leptin receptor expression constructs with or without co-transfection with LRRP expression constructs. Immunoprecipitation with antibodies to P-tyrosine is followed by gel electrophoresis, and blotting. Protein phosphorylation is quantitated by measuring radiation in the size separated proteins with or without LRRP expression construct co-transfection.

X Production of LRRP Specific Antibodies

LRRP substantially purified using PAGE electrophoresis (Sambrook, supra) is used to immunize rabbits and to produce antibodies using standard protocols. The amino acid sequence translated from LRRP is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 5 and 6) is described by Ausubel F M et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring LRR Using Specific Antibodies

Naturally occurring or recombinant LRRP is substantially purified by immunoaffinity chromatography using antibodies specific for LRRP. An immunoaffinity column is constructed by covalently coupling LRRP antibody to an activated chromatographic resin such as CnBr-activated Sepharose (Pharmacia Biotech). After the coupling, the resin is blocked and washed according to the manufacturer's instructions.

Media containing LRRP is passed over the immunoaffinity column, and the column is washed under conditions that allow the preferential absorbance of LRRP (eg, high ionic strength buffers in the presence of detergent). The column is eluted under conditions that disrupt antibody/LRRP binding (eg, a buffer of pH 2–3 or a high concentration of a chaotrope such as urea or thiocyanate ion), and LRRP is collected.

XII Identification of Molecules Which Interact With LRRP

LRRP, or biologically active fragments thereof, are labelled with $^{125}$I Bolton-Hunter reagent (Bolton, A E and Hunter, W M (1973) Biochem J 133: 529). Candidate molecules previously arrayed in the wells of a 96 well plate are incubated with the labelled LRRP, washed and any wells with labelled LRRP complex are assayed. Data obtained using different concentrations of LRRP are used to calculate values for the number, affinity, and association of LRRP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 131 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: HNT2NOT01
        ( B ) CLONE: 492703

( x i ) SEQUENCE DESCRIPTION: SEQ ID NO:1:

```
Met  Ala  Gly  Val  Lys  Ala  Leu  Val  Ala  Leu  Ser  Phe  Ser  Gly  Ala  Ile
 1                  5                        10                       15

Gly  Leu  Thr  Phe  Leu  Met  Leu  Gly  Cys  Ala  Leu  Glu  Asp  Tyr  Gly  Val
              20                       25                       30

Tyr  Trp  Pro  Leu  Phe  Val  Leu  Ile  Phe  His  Gly  Ile  Ser  Pro  Ile  Pro
              35                       40                  45

His  Phe  Ile  Ala  Lys  Arg  Val  Thr  Tyr  Asp  Ser  Asp  Ala  Thr  Ser  Ser
     50                       55                       60

Ala  Cys  Arg  Glu  Leu  Ala  Tyr  Phe  Phe  Thr  Thr  Gly  Ile  Val  Val  Ser
65                       70                       75                       80

Ala  Phe  Gly  Phe  Pro  Val  Ile  Leu  Ala  Arg  Val  Ala  Val  Ile  Lys  Trp
                    85                       90                       95

Gly  Ala  Cys  Gly  Leu  Val  Leu  Ala  Gly  Asn  Ala  Val  Ile  Phe  Leu  Thr
               100                      105                      110

Ile  Gln  Gly  Phe  Phe  Leu  Ile  Phe  Gly  Arg  Gly  Asp  Asp  Phe  Ser  Trp
          115                      120                      125
```

Glu Gln Trp
130

( 2 ) INFORMATION FOR SEQ ID NO:2:

( i ) SEQUENCE CHARACTERISTICS:
        ( A ) LENGTH: 874 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: HNT2NOT01
        ( B ) CLONE: 492703

( x i ) SEQUENCE DESCRIPTION: SEQ ID NO:2:

| | | | | | |
|---|---|---|---|---|---|
| GTCTGGCTTG | GGCAGGCTGC | CCGGGCCGTG | GCAGGAAGCS | GGAAGCAGCC | GCGGCCCCAG | 60 |
| TTCGGGAGAC | ATGGCGGGCG | TTAAAGCTCT | CGTGGCATTA | TCCTTCAGTG | GGCTATTGG | 120 |
| ACTGACTTTT | CTTATGCTGG | GATGTGCCTT | AGAGGATTAT | GGCGTTTACT | GGCCCTTATT | 180 |
| CGTCCTGATT | TTCCACGGCA | TCTCCCCCAT | CCCCCATTTC | ATTGCCAAAA | GAGTCACCTA | 240 |
| TGACTCAGAT | GCAACCAGTA | GTGCCTGTCG | GGAACTGGCA | TATTTCTTCA | CTACTGGAAT | 300 |
| TGTTGTTTCT | GCCTTTGGAT | TTCCTGTTAT | TCTTGCTCGT | GTGGCTGTGA | TCAAATGGGG | 360 |
| AGCCTGCGGC | CTTGTGTTGG | CAGGCAATGC | AGTCATTTTC | CTTACAATTC | AAGGGTTTTT | 420 |
| CCTTATATTT | GGAAGAGGAG | ATGATTTTAG | CTGGGAGCAG | TGGTAGCACT | TTATTCTGAT | 480 |
| TACAGTGCAT | TGAATTTCTT | AGAACTCATA | CTATCTGTAT | ACATGTGCAC | ATGCGGCATT | 540 |
| TTACTATGAA | ATTTAATATG | CTGGGTTTTT | TAATACCTTT | ATATATCATG | TTCACTTTAA | 600 |
| GAAAGACTTC | ATAAGTAGGA | GATGAGTTTT | ATTCTCAGCA | AATAGACCTG | TCAAATTTAG | 660 |
| ATTATGTTAC | TCAAATTATG | TTACTTGTTT | GGCTGTTCAT | GTAGTCACGG | TGCTCTCAGA | 720 |
| AAATATATTA | ACGCAGTCTT | GTAGGCAGCT | GCCACCTTAT | GCAGTGCATC | GAAACCTTTT | 780 |
| GCTTGGGGAT | GTGCTTGGAG | AGGCAGATAA | CGCTGAAGCA | GGCCTCTCAT | GACCCAGGAA | 840 |
| GGCCGGGGTG | GWTCCCTCTT | TKTTTTGTAG | TCCA | | | 874 |

( 2 ) INFORMATION FOR SEQ ID NO:3:

( i ) SEQUENCE CHARACTERISTICS:
        ( A ) LENGTH: 145 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 733888

( x i ) SEQUENCE DESCRIPTION: SEQ ID NO:3:

Met Cys Cys His Ile His Ile Gln Cys Phe Asp Cys Cys Ser Met Lys
1               5                   10                  15

Asn Thr Ile Leu Ala Val Ala Ala Leu Ala Phe Ala Gly Val Val Gly
            20                  25                  30

Leu Thr Phe Leu Val Leu Gly Cys Ala Leu Pro Arg Tyr Gly Thr Trp
        35                  40                  45

Thr Pro Met Phe Val Ile Thr Phe Tyr Val Leu Ser Pro Val Pro Leu
    50                  55                  60

Leu Ile Ala Arg Arg Phe Gln Glu Asp Met Thr Gly Thr Asn Ala Cys

```
    65                      70                       75                      80
Ile Glu Leu Ala Leu Phe Ile Thr Thr Gly Ile Val Ile Ser Ala Phe
                85                      90                      95

Ala Leu Pro Ile Val Leu Ala His Ala Gly Thr Ile Ala Met Ser Ala
            100                     105                 110

Cys Phe Leu Ile Phe Ile Ala Asn Ser Ile Asn Phe Ser Val Ile Ile
            115                 120                 125

Phe Tyr Phe Arg Ile Phe Asn Gly Glu Asp Met Asn Gly Met Ser Leu
        130                 135                 140

Trp
145
```

( 2 ) INFORMATION FOR SEQ ID NO:4:

( i ) SEQUENCE CHARACTERISTICS:
      ( A ) LENGTH: 140 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( A ) LIBRARY: GenBank
      ( B ) CLONE: 1197072

( x i ) SEQUENCE DESCRIPTION: SEQ ID NO:4:

```
Met Met Glu Phe Lys Val Ser Pro Leu Thr Lys Ile Ile Ser Leu Ser
1               5                   10                  15

Gly Phe Leu Ala Leu Gly Phe Leu Leu Val Ile Leu Ser Cys Ala Leu
            20                  25                  30

Phe His Asn Tyr Tyr Pro Leu Phe Asp Ile Leu Ile Phe Leu Leu Ala
            35                  40                  45

Pro Ile Pro Asn Thr Ile Phe Asn Ala Gly Asn Lys Tyr His Thr Ser
        50                  55                  60

Asp Phe Met Ser Asp Ser Ser Asn Thr Gly Gln Asp Leu Ala His Phe
65                  70                  75                  80

Leu Thr Gly Met Leu Val Thr Ser Gly Ile Ala Leu Pro Val Val Phe
                85                  90                  95

Tyr His Cys Gln Leu Ile Gly His Leu Ser Cys Ile Met Cys Met Ile
            100                 105                 110

Gly Gly Leu Ile Ile Tyr Ser Ser Ile Val Ile Phe Lys Trp Phe Phe
            115                 120                 125

Lys Lys Asp Phe Asn Glu Asp Asp Ser Leu Phe Gly
        130                 135                 140
```

I claim:

1. An isolated and purified polynucleotide sequence encoding a polypeptide consisting of the amino acid sequence of SEQ ID NO:1.

2. The isolated and purified polynucleotide sequence of claim 1 from nucleotides $A_{163}$ to $A_{874}$ of SEQ ID NO:2, inclusive.

3. An isolated and purified polynucleotide sequence consisting of the sequence of SEQ ID NO:2.

4. A polynucleotide sequence which is fully complementary to the polynucleotide sequence of claim 1.

5. An expression vector containing the polynucleotide sequence of claim 1.

6. A host cell comprising the expression vector of claim 5.

7. A method for producing a polypeptide consisting of the amino acid sequence of SEQ ID NO:1, the method comprising the steps of:
   a) culturing the host cell of claim 6 to allow expression of the polypeptide; and
   b) recovering the polypeptide from the host cell culture.

* * * * *